United States Patent [19]

Kellett et al.

[11] Patent Number: 5,261,426
[45] Date of Patent: Nov. 16, 1993

[54] HYDROPHILIC FOAM PAD FOR HAIR STYLING

[75] Inventors: George W. Kellett, Cranford; Betty J. Murphy, Upper Montclair, both of N.J.

[73] Assignee: Creative Products Resource Associates, Ltd., North Caldwell, N.J.

[21] Appl. No.: 707,630

[22] Filed: May 30, 1991

[51] Int. Cl.$^5$ ............................................. A45D 24/16
[52] U.S. Cl. ..................................... 132/108; 132/110; 132/202; 424/70; 424/73; 521/52; 252/91; 15/104.93
[58] Field of Search ............... 132/108, 110, 111, 202, 132/203, 204, 205, 208, 320; 521/52; 424/70, 73, ; 252/91, 106, DIG. 3, 5, 7, 13; 15/104.93, 104.94

[56] References Cited

U.S. PATENT DOCUMENTS

| | | | |
|---|---|---|---|
| 2,922,425 | 1/1960 | Lerner et al. | 132/212 |
| 3,088,158 | 5/1963 | Boyle et al. | 15/506 |
| 3,447,181 | 6/1969 | Coker et al. | 15/104.94 |
| 3,597,250 | 8/1971 | Rands, Jr. et al. | 106/291 |
| 3,647,492 | 3/1972 | Chapman et al. | 106/291 |
| 3,833,008 | 9/1974 | Blackett, Jr. | 132/313 |
| 3,935,129 | 1/1976 | Jabalee | 252/525 |
| 4,066,394 | 1/1978 | Leonard | 8/137 |
| 4,127,515 | 11/1978 | MacRae et al. | 521/112 |
| 4,137,200 | 1/1979 | Wood et al. | 521/159 |
| 4,157,388 | 6/1979 | Christiansen | 424/70 |
| 4,206,195 | 6/1980 | Bolich, Jr. et al. | 424/16 |
| 4,269,824 | 5/1981 | Villamarin et al. | 424/70 |
| 4,271,272 | 6/1981 | Strickman et al. | 521/110 |
| 4,273,760 | 6/1981 | Koehler et al. | 424/70 |
| 4,343,910 | 8/1982 | Busch, Jr. et al. | 521/82 |
| 4,344,930 | 8/1982 | MacRae et al. | 424/73 |
| 4,548,954 | 10/1985 | Smith et al. | 521/52 |
| 4,563,483 | 1/1986 | Smith et al. | 521/111 |
| 4,565,644 | 1/1986 | Smith et al. | 252/92 |
| 4,569,861 | 2/1986 | Smith et al. | 427/244 |
| 4,581,385 | 4/1986 | Smith et al. | 521/111 |
| 4,586,518 | 5/1986 | Cornwall et al. | 132/206 |
| 4,594,362 | 6/1986 | Smith et al. | 521/52 |
| 4,719,104 | 1/1988 | Patel | 424/70 |
| 4,741,855 | 5/1988 | Grote et al. | 252/142 |
| 4,806,572 | 2/1989 | Kellett | 521/112 |
| 4,856,541 | 8/1989 | Kellett et al. | 132/110 |

FOREIGN PATENT DOCUMENTS

| | | |
|---|---|---|
| 1229270 | 3/1960 | France . |
| 2015972 | 4/1970 | France . |
| 2179052 | 8/1986 | United Kingdom . |

*Primary Examiner*—Gene Mancene
*Assistant Examiner*—Frank A. LaViola
*Attorney, Agent, or Firm*—Merchant, Gould, Smith, Edell, Welter & Schmidt

[57] ABSTRACT

A hair conditioning and styling pad is provided which comprises a shaped body of a resilient, open-celled, hydrophilic polyurethane foam matrix integrally incorporating an aqueous phase incorporating about 70-90% water, about 5-25% of a hair conditioning agent, and a nonionic surfactant. The pad is preferably affixed to the tines of a styling brush or comb to yield a composite brush or comb which is effective to condition and style hair.

37 Claims, 2 Drawing Sheets

HYDROPHILIC FOAM PAD FOR HAIR STYLING

BACKGROUND OF THE INVENTION

Liquid conditioning agents are commonly employed to enhance the manageability and appearance of the hair of humans and animals. Conditioning agents include materials which are substantive to hair, i.e., which are absorbed onto the hair. Such agents include various modified proteins and other film-forming natural and synthetic polymers. Typically, the hair is thoroughly wetted, an amount of shampoo is manually rubbed into the hair, and the cleaned hair is rinsed. The conditioning agents are then applied to the hair prior to the final water rinse and drying steps.

Hairstyling requires further application of liquid or semi-liquid resins and waxes, which are usually rubbed or sprayed into the hair, or applied after the hair has been wrapped around rollers. The treated hair can then be recurled or otherwise shaped by combing, or brushing in conjunction with a blow dryer. Styling agents, such as mousses and gels, can be extremely sticky and thus difficult to use and apply. Glazes and lotions, on the other hand, are typically runny and messy as mentioned above. Any of these agents may be difficult to dispense uniformly throughout the hair. For this reason, their use may require excessive brushing, which may be inconvenient, uncomfortable, and unduly time consuming. Also, use of the conventional agents may require continued washing of the stylist's hands, since many of the agents are applied manually. Furthermore, they may require considerable skill for effective use.

Styling often includes the use of electric rollers or curling irons. The heat from these items may overly dry the hair, causing damage. This is a particular problem with hair which has been chemically treated, for example, hair which has been dyed or colored.

Hair coloring products are commercially available which may be used to temporarily alter or "refresh" the hair color of humans and animals. Such products have been characterized as "temporary" in that they may be substantially removed from the hair by a single shampooing. Representative temporary hair coloring products are commercially available in the form of water-based lotions, for example, Instant Beauty ™, available from Clairol, Inc., Stamford, Conn.; and Fanci-Full ®, available from Roux Laboratories, Jacksonville, Fla. The lotions may further contain propylene glycol, alcohol, preservatives, and the like, as well as one or more dyes, for example, D&C Green No. 5, D&C Orange No. 4, D&C Red No. 33, D&C Yellow No. 10, Ext. D&C Violet No. 2, FD&C Blue No. 1, FD&C Red No. 4, Direct Black 51, Acid Violet 43, Direct Red 80, and Acid Orange 24.

These lotion-based products are disadvantageous in that they may be difficult to apply thoroughly and evenly throughout the length of the hair, and may run and drip, staining clothing and irritating the eyes of the user. Further, the application of lotionl-based products generally requires the use of a person's hands, so that the lotion can be worked through the hair, as discussed above. Contact of the hair color dye with skin may cause staining, therefore, the wearing of plastic gloves may be necessitated to protect the user's hands. In addition, cotton strips or other absorbent material may be required for placement around the face, at the base of the hair, to absorb lotion which runs or drips out of the hair, and thus prevent contact with the user's eyes or skin.

Temporary hair coloring products are also commercially available in the form of alcohol-based aerosol sprays, for example, Metallics ™ Hair Color, available from E. Davis, Inc., Piscataway, N.J. These novelty-type products may contain metallic pigments to impart an iridescent sheen to the hair. The alcohol in these products may be damaging to hair which is subsequently styled with heating elements such as blow dryers, curling irons, and heated rollers. Furthermore, by nature of these aerosol spray-on application, these products can be accidentally applied to the skin or eyes, causing damage thereto.

One approach to control the delivery of hair conditioning agents is disclosed by Bolich, Jr. et al. (U.S. Pat. No. 4,206,195), wherein a porous substrate, preferably a nonwoven fabric, having thereon a layer of a salt overcoated with a solid layer of conditioner. When wet hair is rubbed with this article, a portion of the salt and the conditioner are transferred to the hair.

Therefore, a need exists for a method which is effective and convenient for rapidly conditioning and/or styling hair, without the problems discussed above. For example, a need exists for a method to effectively, uniformly, and conveniently distribute styling and conditioning ingredients throughout the hair. A further need exists for a method which is effective and convenient to rapidly distribute temporary hair coloring agents throughout the hair, at the same time that the hair is styled and conditioned.

BRIEF DESCRIPTION OF THE INVENTION

The present invention is directed to a conditioner and/or styler, preferably for use on wet or damp hair, which comprises a shaped body of a resilient, open-celled hydrophilic polyurethane foam. The polyurethane foam is formed by reaction of selected prepolymer resins which an aqueous reactant phase, which becomes incorporated into and bonded to the cell walls of the cured foam matrix without substantially occluding the cellular voids. This "interior aqueous phase" is formulated to contain polymeric conditioning agents and surfactants. As used herein, the term "conditioning agent" is intended to encompass those resins or polymers which are the active ingredients in the liquid or semi-liquid agents that are commonly referred to in the art as "conditioners," "stylers," or mixtures thereof. The term does not include, and the present pads do not contain, natural or synthetic emollient oils, fats or waxes such as those disclosed to be essential by MacRae et al. (U.S. Pat. No. 4,344,930). These include higher fatty alcohols and vegetable oils.

In an embodiment of the invention disclosed in commonly assigned U.S. Pat. No. 5,002,075, the aqueous phase can include one or more temporary hair coloring agents, in addition to the conditioning agents and surfactants. In this color-modified aqueous phase, the temporary hair coloring agents are present in an amount effective to color a portion or all of the hair of the user, as desired. As used herein, the term "temporary" with respect to a hair coloring agent is intended to mean that the hair coloring agent can be substantially removed from the user's hair by a single shampooing. However, the present foam styling and/or conditioning pads do not require dyes, coloring agents, tints or mineral pigments.

The conditioning agents and surfactants are present in the aqueous phase or the color-modified aqueous phase in amounts which are effective to condition and/or style the hair when the foam body is contacted with wet or damp hair. Additional optional ingredients which can be dispersed in the aqueous reactant phase and incorporated into the foam body include particulate absorbents, fragrances, antimicrobial agents, insecticides and the like.

In order to condition and/or style dry hair, foam pads having the agents of the invention therein are attached to conventional rollers, curling irons and the like. With respect to rollers, this is done by passing tines or bristles of the rollers through the pads. The use of these pads with electric rollers or curling irons reduces the likelihood of hair damage.

Preferred foam pads prepared in accord with the invention are resilient and possess an open-celled matrix which is highly reticulated in the sense that the area occupied by cell walls is relatively small compared to the total cellular volume. These characteristics permit the pad to effectively contact the individual hairs, and to release an amount of the interior aqueous phase effective to deposit effective amounts of conditioning and styling agents on the hair, or to release an amount of the interior color-modified aqueous phase effective to deposit an effective amount of temporary hair coloring agent on the hair, in addition to the conditioning and styling agents.

It is also advantageous to incorporate a minor amount of an inorganic salt such as sodium chloride (NaCl) into the aqueous phase, or the color-modified aqueous phase. Surprisingly, it was found that about 0.05-2.5% of NaCl substantially increased the amount of the aqueous phase which was released from the foam matrix during use, without unduly irritating the skin of the user.

As used herein, the term "pad" is intended to encompass any shaped foam body which is useful for manual application to the hair, including sticks, blocks, strips, sheets and discs of hydrophilic foam. As used herein with respect to the pads intended for hair coloring, the words "colored" or "color-modified" mean that an aqueous phase which is foamed to form the pads includes a temporary hair coloring agent, in addition to the styling and/or conditioning ingredients. The term "resilient" is intended to indicate that the pads maintain their integrity during use, i.e., are not friable. Although wet or damp hair can be conditioned and/or styled (and optionally colored) by rubbing it manually with the pad, it is highly preferable that an appropriately sized pad be impaled on the tines of a conventional styling brush. Thus secured, the pad can effectively contact the hair when the hair is brushed by the user.

Thus, the styling brush or roller and the pad secured thereon form novel composite conditioning, styling and coloring devices which are also an embodiment of the present invention. Preferred pads for use in conjunction with commercially available styling brushes are shaped into rectangular or cylindrical blocks. These pads comprise cells which substantially vary in diameter and which also comprise a substantial number of large cells, e.g., cells which are about 1.0-5.0 mm in diameter. This open, highly reticulated structure permits the foam pad to be easily affixed to the styling brush by the user, since the relatively rigid tines of the brush can readily pass entirely through the foam pad.

Color-modified pad/styling brush arrangements according to an embodiment of the present invention are particularly useful for thorough, even application of the coloring, conditioning, and styling agents to substantially all the hair of the user, if desired. In alternative arrangements incorporating the temporary hair coloring agent, the pad may be shaped as an elongated strip, suitable for impaling on the teeth of a comb, or the pad may be shaped as a small disc or block which may be impaled on a pointed stick or rod. Another alternative arrangement is one in which a relatively small cone or tuft of the color-modified foam pad is attached to an immovable or a retractable base, in the same manner as a felt-tip "pen" or similar arrangements which are commercially available and which are used to provide for controlled application of nail polish or nail polish remover. These types of arrangements may be advantageously used for "touch-up" applications of temporary hair color; for example, to impart color only to the roots of the hair, or to create a "streaked" effect in the user's hair.

The finished pads will incorporate a high weight percentage of aqueous reactant phase to polymeric foam matrix, e.g., a ratio of aqueous reactant phase:prepolymer resin of up to about 3:1 can be employed. For color-modified pads, the ratio of aqueous reactant phase:prepolymer resin is preferably about 2:2.5:1. However, due to the high affinity of the interior aqueous phase for the matrix fibrils, the finished pads are only slightly slick to the touch and can help to dry the hair during use. The hair is conditioned and/or styled in the sense that hair body, sheen and curl retention are imparted or improved. If the pads incorporate a temporary hair coloring agent in addition tro the styling and conditioning ingredients, hair color and sheen are also imparted, or "renewed" or "refreshed."

In contrast to foam pads such as the wax-containing pad disclosed by MacRae et al. (U.S. Pat. No. 4,127,515) which must be moistened prior to use, the addition of excess water to the present pads prior to use on wet hair would be deleterious in that the added water would tend to dilute the interior aqueous phase. Furthermore, the addition of excess water as described by MacRae et al. over and above the amount of water typically present in a user's wet hair would destroy the ability of the present pad to release the interior aqueous phase in a controlled fashion, leading to dripping and running during use. The ability of the pads to dry wet or damp hair, as described below, would also be lost.

Although the treated sheets disclosed by Bolich, Jr. et al. (U.S. Pat. No. 4,206,195) are disclosed to be useful when applied to wet hair, the use of a releasable interior aqueous phase in the present pads provides a more uniform application of the active ingredients, while avoiding the need to select actives that are solids at room temperature. Furthermore, the present pads can be used on dry hair, since the addition of limited amounts of water, such as that present in a user's wet hair, is not deleterious of the present foam pads, but rather, can assist the release of the interior aqueous phase therefrom. Therefore, by moistening the brush-pad composite with water, and brushing it through dry hair, control and hold are enhanced, achieving the effect of a hair spray or similar fixative.

In contrast to the hair cleaning and conditioning foam pads disclosed in commonly assigned U.S. Pat. No. 4,856,541, the present pads do not contain significant amounts of organic solvents.

All percentages are weight percentages unless otherwise indicated. Percentages of commercially available materials, such as surfactants, have been adjusted downward, if necessary, so that they represent only the active component or components, and do not include water or other solvents. Common chemical names of ingredients are given in accord with the *CTFA Cosmetic Ingredient Dictionary*, the Cosmetic, Toiletry and Fragrance Assoc., Inc., Pub., Washington, D.C. (3d ed. 1982, and 3d ed. supp. 1985), the relevant disclosures of which are incorporated by reference herein.

As used herein, the phrase "consisting essentially of" indicates that the material in question will include the recited ingredients or components, plus only those additional components which would not produce a deleterious effect or materially affect the basic and novel characteristic of the material.

BRIEF DESCRIPTION OF THE DRAWINGS

The drawings constitute a part of the specification and include exemplary embodiments of the present invention, while illustrating various objects and features thereof. In some instances, relative material thicknesses, and sizes, may be shown exaggerated to facilitate an understanding of the invention.

DETAILED DESCRIPTION OF THE INVENTION

The hair conditioning and/or styling pads of the present invention are prepared by a process comprising forming an aqueous dispersion comprising a nonionic surfactant and a polymeric hair conditioning agent. As defined herein, the hair conditioning agent is intended to encompass those polymers or resins which are the active ingredients in the liquid or semi-liquid agents commonly referred to in the art as "conditioners," "stylers," or mixtures thereof. Optional ingredients which can be incorporated in the aqueous dispersion include a temporary hair coloring agent, an inorganic salt, a cationic surfactant, a particulate absorbent and a silane coupling agent, biocides, fragrance and preservative. The fully-formed aqueous dispersion is then combined with a water-foamable prepolymer resin, and the reaction mixture allowed to foam and cure, to yield a self-crosslinked, open-celled, resilient polyurethane foam body. The foam may be cured to the desired final shape in an appropriately formed mold, or may be cut into the end-use configuration from a larger body.

Prepolymer Resins

A commercially available class of water foamable prepolymer resins which yield cross-linked, hydrophilic polyurethane foams upon the addition of stoichiometric excesses of water are those belonging to the Hypol ® series (W. R. Grace & Co., Lexington, Mass.; FHP 5000, 4000, 3000, 2000, 2000 HD, 2002) which are generally described in U.S. Pat. No. 4,137,200 and in the W. R. Grace & Co. technical bulletins, *Hypol* ® and *Hypol Plus* ® *Foamable Hydrophilic Prepolymers*, the disclosures of which are incorporated by reference herein. These liquid resins are prepared by capping mixtures of low molecular weight polyols having 3–8 hydroxyl groups and polyoxyethylene diols with toluene diisocyanate. The capped alcohol mixtures have an average number of free isocyanate groups per molecule which is equal to two or more, e.g., 2 to 8.

These resins possess molecular weights within the range of about 1300–1400 and have about 1.5–2.6 mEq/g of free isocyanate groups. Upon being contacted with a molar excess of water, the isocyanate groups hydrolyze to release carbon dioxide gas, thus foaming the resin without the need for added catalysts or blowing agents. The free amino groups formed by the hydrolysis reaction react with unhydrolyzed isocyanate groups to form ureido groups which cross-link and stabilize the foam, while entrapping a part of the excess water in the cell walls, where it acts to impart hydrophilic properties to the foam. The compatibility of the foam matrix with large molar excesses of water is a necessary requirement of resins useful in the practice of the present invention, since large amounts of water are needed to uniformly introduce large amounts of absorbents, surfactants and conditioning agents into the matrix.

Other poly-$C_2$-$C_3$-alkylenoxy glycols capped with aromatic isocyanates may be prepared which possess a suitable balance between their extent of cross-linking prior to foaming and their ability to cross-link or to further cross-link during foaming (due to the presence of more than two reactive isocyanate groups per resin molecule), so as to be useful in the practice of the present invention over the entire range of conditioner and surfactant content. These prepolymer resins are prepared by polymerizing ethylene oxide to yield polyalkylenoxy polyols having a molecular weight of about 900–1100. These polyols are reacted with a stoichiometric excess of a polyisocyanate. Suitable isocyanate include toluene diisocyanate, triphenylmethane-4,4′,4″-triisocyanate, benzene-1,3,5-triisocyanate, hexamethylene diisocyanate, zylene diisocyanate, chlorophenylene diisocyanate and mixtures thereof. The useful resins recovered have a somewhat lower number of mEq of free isocyanate groups (NCO) per gram of resin than do the Hypol ® resins, e.g., 1.3–1.5 mEq/g, and can exhibit substantially higher tensile strengths when foamed and cured at or near ambient temperatures.

Commercially available self-crosslinking resins include Trepol ® A-62 and TRE STD ® prepolymer resin (Twin Rivers Engineering Co., East Booth Bay, Me.), which form acceptable foams upon reaction with at least a stoichiometric excess of water, without employing a low molecular weight polyol component to raise the average number of free isocyanate groups per glycol ether molecule to above two. TRE STD ® resin has an average free isocyanate content of about 1.4 mEq/g, comprises a polyol component having an average molecular weight of about 1000, exhibits a viscosity at 32° C. of 4700 cps and solidifies at 15.5° C.

In the practice of the present invention, useful foams may be formed employing a weight ratio of water (i.e., aqueous phase) to prepolymer resin of about 3.0–1.01:1, preferably about 2.5–1.5:1, and more preferably about 2.3–1.75:1. If a temporary hair coloring agent is incorporated into the aqueous phase, the ratio of aqueous phase:prepolymer resin is preferably about 2.5–2:1. These ranges represent mole ratios of water to free isocyanate groups of about 20–150:1, preferably about 30–135:1.

These amounts of water react with the free isocyanate groups to release carbon dioxide, which blows the prepolymer into a cross-linked, open-celled foam which is rendered hydrophilic by the integral entrapment of excess water in the cell walls of the foam matrix. When the prepolymer-slurry mixture is allowed to set in molds, a flexible, resilient foam body of the desired shape is formed.

Polymeric Conditioning Agent

The aqueous reactant phase will also be formulated to comprise an effective amount of a conditioning agent which, as noted above, can also function to style or fix the hair of the user. Useful conditioning agents include film-forming polymers which are water-soluble water-dispersible, and which are substantive to the hair, in that they are absorbed by the hair. The bound conditioners act to modify the properties of the hair, i.e., to improve its feel, manageability, combability, body, sheen and to repair split ends. The conditioning agents can also function as fixatives, to allow the user to style the hair, e.g., to curl, wave or otherwise shape the hair. Since a primary function of the present pads is to condition and/or style the hair, the aqueous reactant phase will contain large amounts of one, or preferably, a plurality of conditioning agents, e.g., up to about 25% by weight.

One useful conditioner is hydrolyzed animal protein. These collagenous materials are commercially available under a variety of designations, e.g., as Nutrilan ® (Henkel Corp., Ambler, Pa.; m.w. 500–2000) or Peptein ® 2000 (Hormel & Co., Austin, Minn.; 55% min. solids, pH 5.8–6.3). Collagen derivatives in which collagen has been chemically modified to attach cationic groups thereto are also useful as conditioners in the present invention. They include lauryldimonium droxypropylamino hydrolyzed animal protein (Lamequat ® L, Henkel Corp., m.w. 600–700); and protein abietic acid condensate, triethanol amine salt (CTFA: TEA-Abietoyl-Hydrolyzed Animal Protein (Lamepon ® PA-TR, Henkel Corp.)).

Other collagen derivatives which can be employed as conditioners include potassium undecylenoyl hydrolyzed animal protein, which can also function as an antidandruff agent (Lamepon ® UD, Henkel Corp.); potassium coco-hydrolyzed animal protein (Lamepon ® S, Henkel Corp.); and triethanolamine-cocohydrolyzed animal protein (Lamepon ® S-TR; Henkel Corp., m.w. 790–890, 11–13% protein; and Lamepon ® ST 40; Henkel Corp., m.w. 790–890, 14–16% protein). The aqueous reactant phase can incorporate about 0.025–7.5%, preferably about 0.1–5% of these collagenous conditioners.

Other useful cationic polymeric conditioning agents include about 0–5%, preferably about 0.5–3% of cationic cellulosic polymers. These materials are available as Celquat ® H-100, H-200 and L-200 (National Starch & Chem. Corp., Bridgewater, N.J.). The Celquat ® products can function both as conditioners and stylers.

Other totally synthetic organic polymeric compounds can be employed, primarily for their fixative, or styling, properties. These include about 0–2.5%, preferably about 0.25–2% of vinylpyrrolidone-based polymers or copolymers ("PVPs"), e.g., vinylpyrrolidone/-dimethylaminoethylmethacrylate copolymer. This copolymer is available from GAF Corp. (Wayne, N.J.) as Gafquat ® 755N polymer (high molecular weight). Another useful PVP-type polymer is Gaffix ® VC-713 (vinylcaprolactam/vinylpyrrolidone/dimethyaminoethylmethacryate copolymer). Other useful cationic film-forming resins from GAF include about 1–10% of vinylpyrrolidone/vinyl acetate copolymers, i.e., PVP/VA E-735 (mole ratio 70/30); PVP/VA E-635 (mole ratio 60/40) PVP/VA E-535 (mole ratio 50/50) and PVP/VA S-630; about 1–5% of water-soluble vinylpyrrolidone alkene copolymers (Ganex ® P-904); and about 1–10% of polyvinylpyrrolidones, available as PVP K-30 (m.w. 40,000), PVP K-60 (m.w. 160,000), and PVP K-90 (m.w. 360,000).

Up to about 2.5%, preferably about 0.1–2.0% of amino-functionalized polydimethyl siloxanes can also be employed as cationic polymeric conditioning agents, e.g., Dow Corning ® 929 Cationic Emulsion (35% silicone content, pH 7.6).

The conditioning agent can also be combined with an effective amount of a plasticizer, such as acetin, diacetin and triacetin.

Surfactant

One or more foam-reticulating surfactants will also be incorporated into the aqueous phase. These surfactants function to remove the window membranes of foam cells, thus producing the desired reticulated, or highly open, structure. The surfactant also enhances the cleaning power of the foam by dispersing oily or greasy soils when the foam is brought into contact with the hair. Foam reticulating surfactants are preferably nonionic surfactants which optionally can include cationic surfactants.

Useful nonionic surfactants include the polyoxyalkylene block copolymers formed by condensing ethylene oxide with a hydrophobic polyoxyalkylene base formed by the condensation of propylene oxide with propylene glycol. The hydrophobic portion of these compounds has a molecular weight sufficiently high so as to render it water-insoluble. The addition of polyoxyethylene moieties to this hydrophobic portion increases the water solubility of the molecule as a whole, and the liquid character of the product is retained up to the point where the polyoxyethylene content is about 50% of the total weight of the condensation product.

Examples of compounds of this type include certain of the commercially available Pluronic ® surfactants (CTFA designation: Poloxamer series, BASF Wyandotte Corp., Wyandotte, Mich.). Preferably, those in which the polyoxypropylene ether has a molecular weight of about 1750–2250 and the polyoxyethylene content is about 40–60% of the molecule by weight, e.g., Pluronic ® P-75, P-85, and P-65. These surfactants are believed to contribute to the desirable nonuniform cell size of the cured foam which also retains the necessary tensile strength. "Low polyoxyethylene" poloxamers, e.g., ones in which the polyoxyethylene content is about 10–30% of the molecule by weight, do not function effectively, since they produce foam matrices which are overly weak, possibly due to a deleterious interaction with the large amounts of cationic conditioners which are employed. Such surfactants include Pluronic ® L-62.

Although it is preferred that the nonionic surfactant component of the aqueous reactant phase contain only polyoxyalkylene block copolymers of the poloxamer type, a variety of other nonionic surfactants can be used in combination with the polyoxyalkylene block copolymers. Other water-soluble, nonionic surfactants which are useful in the present invention include the polyoxyalkoxylated lanolins and the polyoxyalkoxylated fatty alcohols. The polyoxyalkoxy chains preferably will comprise mixed propylenoxy and ethylenoxy units. The lanolin derivatives will typically comprise about 20-70 such lower-alkoxy units while the $C_{12}$-$C_{20}$-fatty alcohols will be derivatized with about 8-15 lower alkyl units. One such useful lanolin derivative is Lanexol AWS ® (PPG-12-PEG-50) of the general formula Lanolin[OCH(CH$_3$)CH$_2$]$_x$(OCH$_2$CH$_2$)$_y$OH, wherein x is about 12 and y is about 50 (Croda, Inc., New York, N.Y.). A useful poly(15-20)$C_2$-$C_3$-alkoxylate is PPG-5-Ceteth-20; CH$_3$(CH$_2$)$_{14}$CH$_{2[OCH(Ch3)}$CH$_2$]$_x$(OCH$_2$CH$_2$)$_y$OH wherein x is about 8 and y is about 2 (Procetyl AWS ®, Croda, Inc.). In some instances, a combination of these two classes of surfactants can be used to replace poloxomer-type surfactants.

Other useful nonionic surfactants for use in the present invention are the alkanol amides of ($C_{10}$-$C_{22}$) fatty acids, preferably, the diethanolamide, monoisopropanolamide or monoethanolamides of ($C_{12}$-$C_{18}$) fatty acids. These compounds are commercially available as the Standamid ® series (Henkel Corp.), e.g., lauramide DEA, cocamide DEA and cocamide MEA. Other useful compounds of this type include stearamide MEA, stearamide MIPA, stearamide DEA, myristamide DEA, myristamide MEA, myristamide MIPA and the like.

A further class of nonionic surfactant that can be used in the present invention, preferably in combination with a polyoxyalkylene block copolymer, is the silicone glycol copolymers of general formula: (CH$_3$)$_3$Si—O—[-Si(CH$_3$)$_2$O]$_x$[Si(CH$_3$)(CH$_2$)$_3$(OEt)$_m$(OP$_r$)$_n$OH]-Si(CH$_3$)$_3$, wherein x, n and m are adjusted so that the surfactants are water-miscible and exhibit a viscosity at 25° C. of about 1000-2000. These materials are available from Dow Corning Corp., Midland, Mich., as Dow Corning ® 190 surfactant. About 0.25-5% of these surfactants can be used.

Another useful class of nonionic surfactants is the fatty acid esters of $C_2$-$C_5$-polyols, e.g., the ($C_8$-$C_{22}$) fatty acid monoesters of glycerol, propylene glycol, ethylene glycol, sorbitol and the like. For example, glyceryl monostearate is commercially available as Cerasynt ® 945 from Van Dyk & Co., Belleville, N.J.

Other useful nonionic surfactants include the condensation products of $C_8$-$C_{22}$ alkyl alcohols with 2-50 moles of ethylene oxide per mole of alcohol. Examples of compounds of this type include the condensation products of $C_{11}$-$C_{15}$ fatty alcohols with 3-50 moles of ethylene oxide per mole of alcohol which are commercially available from Shell Chemical Co., Houston, Tex., as, e.g., Neodol ® 23-6.5 ($C_{12}$-$C_{13}$ fatty alcohol condensed with about 7 moles of ethylene oxide), the Poly Tergent ® SLF series from Olin Chemicals or the Tergitol ® series from Union Carbide, e.g., Tergitol ® 15-S-15, which is forced by condensing about 15 moles of ethylene oxide with a $C_{11}$-$C_{15}$ secondary alkanol; and Tergitol ® TMN-6, which is the condensation product of about 6 moles of ethylene oxide with isolauryl alcohol (CTFA name: isolaureth-6). Another commercially available nonionic surfactant of this class is the condensation product of lauryl alcohol with about 11-40 moles of ethylene oxide, e.g., Lipocol ® L-23 (OEt$_{23}$, Lip Chemicals, Inc., Paterson, N.J.).

Other nonionic surfactants which may be employed include the ethylene oxide esters of $C_6$-$C_{12}$ alkyl phenols such as (nonylphenoxy)polyoxyethylene ether. Particularly useful are the esters prepared by condensing about 8-12 moles of ethylene oxide with nonylphenol, e.g., the Igepal ® CO series (GAF Corp., New York, N.Y.).

Other useful nonionics include the ethylene oxide esters of alkyl mercaptans such as dodecyl mercaptan polyoxyethylene thioether, the ethylene glycol esters of fatty acids such as the lauric ester of polyethylene glycol and the lauric ester of methoxypolyethylene glycol, the ethylene oxide ethers of fatty acid amides, the condensation products of ethylene oxide with partially fatty acid esters of sorbitol such as the lauric ester of sorbitan polyethylene glycol ether, and other similar materials, wherein the mole ratio of ethylene oxide to the acid, phenol, amide or alcohol is about 5-50:1.

Cationic surfactants can optionally be employed in combination with the nonionic surfactants, and are preferably selected from the general class of ammonium salts which possess both surface-active and conditioning properties. Such components can be represented by the general formula (I) below, where R represents a lipophilic group such as a long-chain, ($C_{12}$-$C_{22}$)alkyl, alkylamido, alkylamidoalkyl or polycylic radical, as well as their derivatives; R$_1$, R$_2$, R$_3$ represent H, benzyl, ($C_1$-$C_3$)alkyl, hydroxyalkyl or heterocyclic groups, A— is a counter ion such as acetate, tosylate, Cl—, SO$^-_4$, Br—, PO$_4^{+3}$ and n is 1-3.

$$[(R)(R_1)(R_2)(R_3)N]_n{}^+ A^- \qquad (I)$$

Especially preferred compounds are the $C_{12}$-$C_{22}$ alkyl(trimethyl)ammonium halides such as cetrimonium bromide, cetrimonium chloride (Dehyquart ® A, Henkel Corp.), cetrimonium tosylate, laurtrimonium chloride and the like.

Amphoteric detergents may also be incorporated into these hydrophilic foams. Preferred amphoteric surfactants are substantive to the hair and impart antistatic properties thereto. These detergents will be employed in a compatible proportion and manner with the nonionic surfactants.

Anionic surfactants will generally not be incorporated into the present foams, since their detergency is not required, and since they would be likely to interact deleteriously with the large amounts of cationic conditioners. The present aqueous phases are formulated so that they can be used on wet or dry hair without producing detergent foam.

Temporary Hair Coloring Agents

Useful temporary hair coloring agents of the present invention are those which comprise composite pigments or mineral oxides. As used herein, "composite pigments" refer to pigments which comprise one or more colored ingredients, such as a colored metal oxide or a dye, bonded to or otherwise in association with a substrate. Composite pigments include, for example, the "lakes" which are inorganic salts or dyes in association with an alumina substrate. The "mineral oxides" referred to herein include natural or synthetic oxides of iron, titanium, zinc, chromium, and other minerals. The "dyes" referred to herein include the permitted colors certified by the Food and Drug Administration for use in cosmetics, including FD&C dyes, D&C dyes, and external D&C dyes, as well as non-certified colors.

Representative of the composite pigments which may be utilized as the temporary hair coloring agent of the present invention are those of the Chroma-Lite ® and Spectra-Pearl ® series, commercially available from Van Dyk & Co., Belleville, N.J. The composition and production of the Chroma-Lite ® pigments is described in detail in U.S. Pat. Nos. 3,597,250, issued Aug. 3, 1971, and No. 3,647,492, issued Mar. 7, 1972, the disclosures of which are incorporated by reference herein. Briefly, the Chroma-Lite ® pigments are formed from colored pigments bonded to a pearlescent substrate comprising fine platelets of mica, on the surface of which is an epitaxial deposit of bismuth oxychloride (BiOCl). The weight percentage of BiOCl in the substrate may range from about 10–75%. The finished composite pigments have a pearl-like, velvety, or soft, satiny luster, which is minimally iridescent. Finely divided, insoluble, colored pigments, for example, red oxide, umber, manganese violet, or carmine, can be adhesively bound to the mica/BiOCl substrate by means of a binder. The binder may be a fatty acid salt, a polymeric acid salt, or a silicic acid salt of a multivalent metal; or a water-dispersible polymer such as the commonly available polyvinyl acetate "white glues," e.g., "Elmer's Glue." For example, calcium stearate, the calcium salt of stearic acid, is used as the binder in the Chroma-Lite ® pigments commercially available from Van Dyk. Spectra-Pearl ® pigments, also available from Van Dyk, differ from the Chroma-Lite ® pigments in that the insoluble colored pigments are bound to a substrate formed from the highly refractive titanium dioxide ($TiO_2$) deposited on mica, instead of the substrate comprising BiOCl deposited on mica.

Other composite pigments useful in the present invention include the "lakes," which are aluminum or calcium salts of FDA-certified dyes extended on a substrate of alumina. For example, carmine is the aluminum lake of the natural coloring agent cochineal, derived from insects.

Representative of the mineral oxides useful as the temporary hair coloring agent of the present invention are the Cosmetic Iron Oxides available from Whittaker, Clark and Daniels, Inc., South Plainfield, N.J. As used in the art, "Iron Oxides" refers to an inorganic compound including any one or combinations of synthetically prepared iron oxides, including the hydrated forms. For numerous examples of Iron Oxides, see C.T.F.A. Cosmetic Ingredient Dictionary, 3rd Ed., N. F. Estrin et al., eds. (1982) at pages 131–133, the disclosure of which is incorporated by reference herein.

In general, the temporary hair coloring agents useful in the present invention are those which will remain substantially stable and can be dispersed in water-based systems, and which will not decompose during preparation of the present foam pads at elevated temperatures. If the present pads are formulated so as to temporarily color the hair, the aqueous reactant phase will contain a significant amount of one or more temporary hair coloring agents, e.g., about 5–25% by weight, preferably about 10–20%.

Particulate Absorbent

In some instances, it will be desirable to incorporate a particulate absorbent agent into the aqueous phase employed to form the present foam pads. For example, about 1–20%, preferably about 2–15% of an absorbent mineral powder can help to dry wet or damp hair and can help to impart a sheen to brushed hair via a polishing action. It is to be understood that this mineral powder is to be distinguished from, and is not intended for the same purpose as the mineral oxides or composite pigments which may act as, temporary coloring agents in the present aqueous phase.

Preferably, the absorbent mineral solids will be selected from one or more soft mineral solids (hardness 0.5-1 to 5-5.5). Soft mineral abrasives useful in the present invention include diatomaceous earth, wollastonite, gypsum, calcite, fluorite, cryolite, apatite, kaolinite clays, e.g., kaolin, kaolinite, anauxite, metakaolinite and the like.

Silane Coupling Agent

In the case of optional mineral absorbents such as silicates and aluminates which contain free Si—OH or Al—OH groups, it is preferable to covalently-bond the particulate minerals to the cured polymeric foam matrix via a minor amount of a silane coupling agent. The silane coupling agent functions to bond to both the polyurethane matrix and the surface of the particles of the mineral absorbent, thus chemically coupling the mineral particles into the polymeric matrix and preventing the particles from separating from the foam matrix during the packaging or use. Silane-bound solid particles also clump less readily and so are more evenly dispersed throughout the matrix during foaming.

Useful silane-coupling agents may be selected from members of organosilicon monomers such as aminoalkyl(trisalkoxy)silanes which are characterized by the formula R—$SiX_3$, wherein R is an organofunctional group attached to silicon in a hydrolytically stable manner and X designates hydrolyzable groups which are converted to silanol groups upon hydrolysis. Most commonly, R comprises a 3-aminopropyl or 3-ureidopropyl moiety which may be further separated from the silicon group by one or two—$NH(CH_2)_n$ moieties wherein n=1-2. Preferably, X is an alkoxy group selected from the group consisting of methoxy, ethoxy, 2-methoxyethoxy or is acetoxy. Preferred silane-coupling agents are commercially available from Union Carbide as the A1100-A1160 series, which includes 3-aminopropyl(triethoxy)silane, 3-aminopropyl(trimethoxy)silane (also available from Dow Corning as Z-6020), N-2-aminoethyl-3-aminopropyl-trimethoxysilane, or 3-ureidopropyl-triethoxysilane.

A slurry of the mineral particles is preferably prepared with about 50–70% by weight of the total water used to form the aqueous phase. The aqueous slurry is then treated with an amount of the silane-coupling agent equal to about 0.1–5% by weight of the amount of slurried solid. Completion of the hydrolysis reaction is assured by warming the slurry to at least about 21°–32° C., at which point the other components of the aqueous phase may be added, along with the remainder of the water. When the solid particles are coated in this fashion, the free. amino groups of the coupling agent bind to the polymeric chains of the substrate during the foaming step, i.e., when the aqueous reactant phase and the polyurethane prepolymer resin are mixed together.

Inorganic Salt

It has been found desirable to dissolve a small amount of an inorganic salt in the aqueous reactant phase to facilitate release of the interior aqueous phase from the foam. Such salts include alkali metal and alkaline earth metal salts such as halides, sulfates, carbonates, bicarbonates, phosphates and the like, e.g., NaCl, KCl, LiCl, $CaCl_2$, NaI and the like.

Antimicrobial Agent

Minor but effective amounts of chemically compatible antimicrobial agents may also be included in the present aqueous phases to reduce or eliminate the bioburden of the foam pads during storage and following exposure to air.

Such agents include $C_1$-$C_5$-parabens (para-hydroxy-($C_1$-$C_5$)alkylbenzoates), quaternary ammonium salts (benzalkonium chloride, benzethonium chloride, methylbenzethonium chloride, cetalkonium chloride), 2-nitro-2-bromo-1,3-propanediol, cresol, chlorhexidine digluconate, hydantoin derivatives such as Glydant ® (Glyco), and the like.

The amount of any given antimicrobial agent or mixture thereof included will be dependent upon its potency and stability, but generally will not exceed about 1.0% by weight of the aqueous phase.

Fragrance

Minor but effective amounts of fragrance selected so as to be chemically compatible with the above-described ingredients are preferably included in the compositions of the present invention for cosmetic purposes. Useful fragrances will include, for instance, about 0.025-2%, preferably about 0.05-1.5%, of floral oils such as rose oil, lilac, jasmine, wisteria, apple blossom or compound bouquets such as spice, aldehydic, woody, oriental and the like.

Dermatological Agent

Minor but effective amounts of agents which can control skin conditions such as dandruff and psoriasis can also be incorporated into foam pads and pad-comb composites intended for human use. Therefore, up to about 2.5% of these agents can be incorporated in the aqueous phase. Useful dermatological agents include zinc pyrithione, chloroxine, acetylsalicylic acid, selenium sulfide, undecylenic acid and the like.

Insecticidal Agent

Minor but effective amounts of agents which can control or eliminate fleas, ticks and other pests when applied topically to the hair of an animal, such as a dog or cat, can also be incorporated into the present foam pads and pad-comb composites. Such agents include organophosphorus compounds and carbamates, as well as methoxychlor, rotenone and the pyrethrins. Useful organophosphorus insecticides include methyl parathion, diazinon, malathion and phorate. Useful carbamates include carbaryl, carbofuran, propoxur, methomyl and aldicarb. Useful pyrethrins include allethrin, resmethrin, permethrin and fenvalerate. Due to the widely varying bioactivities of these compounds, the amount to be incorporated into the aqueous phase in order to achieve the release of an effective amount upon application of the pad or pad-comb combinations to the coat of a given animal will necessarily vary, and will be determined by empirical experiments, as would be recognized by one of skill in the art of veterinary medicine.

Preferred Formulations

Therefore, a preferred aqueous reactant phase will comprise about 70-90%, preferably about 75-85%, of water; about 5-25%, preferably about 10-20%, of a polymeric organic conditioning agent; about 0.1-10%, preferably about 0.25-4.5-5%, of a nonionic surfactant; and optionally about 0.1-2.5%, preferably about 0.25-2.25%, of an inorganic salt. Most preferably, the polymeric organic conditioning agent of the aqueous reactant phase will comprise about 50-100% of one or more "stylers," such as cationic cellulosic polymers, vinylpyrrolidone-based polymers or copolymers ("PVPs"), or amino-functionalized polydimethyl siloxanes. If a temporary hair coloring agent is incorporated into the aqueous phase, the amount of water in the aqueous phase is reduced from the amount by which it is present in formulations which do not contain a temporary coloring agent. Therefore, a preferred aqueous reactant phase which includes a temporary hair coloring agent will comprise about 60-80%, preferably about 65-75%, of water; about 5-25%, preferably about 10-20%, of a temporary hair coloring agent; about 5-25%, preferably about 10-20%, of a polymeric organic conditioning agent; about 0.1-10%, preferably about 0.25-5%, of a nonionic surfactant; and optionally 0.1-2.5%, preferably 0.25-2.25% of an inorganic salt.

Whether or not color-modified, the aqueous reactant phase can optionally also include about 0.5-2.5% of a cationic surfactant, about 1-20% particulate soft mineral absorbent and about 0.1-5% by weight of the absorbent of a silane-coupling agent. The aqueous reactant phase can optionally also include minor but effective amounts of preservative, fragrance, antidandruff and/or insecticidal agent. The aqueous phase will not include any significant amounts of water-immiscible organic solvents or of any waxes, e.g., hydrophobic natural waxes or synthetic hydrocarbon waxes.

Preparation

The preparation of an aqueous reactant phase containing an optional particulate mineral absorbent and a silane-coupling agent is described above under Silane Coupling Agent. Generally, the entire amount of water is charged into a suitable mixing vessel. Any cellulose-based polymeric conditioning agent is added at this point and dissolved with agitation and heating, as necessary. The reaction mixture is then maintained at about 25°-30° C. and the nonionic surfactant is added. After dissolution of this ingredient has been achieved, the inorganic salt and the synthetic polymeric or collagen-based conditioning agents are added. The preservative, antidandruff and/or insecticide is also added at this point with continuous agitation.

If desired as an ingredient, the temporary hair coloring agent is added last, with continuous agitation. In typical applications in which a temporary hair coloring agent is added, agitation is continued until the hair coloring agent is completely and evenly dispersed throughout the aqueous phase.

A predetermined amount of the finished aqueous reactant phase is then measured into an appropriately sized mixing vessel and stirred slowly under ambient conditions. To the aqueous phase is added a predetermined amount of prepolymer resin, which preferably has been heated to about 35° C.–40° C. Stirring is increased as the foaming reaction begins and the viscosity of the mixture increases. After about 5-20 sec., the foaming mixture is poured into appropriately sized molds which are covered as soon as full rise is achieved. Due to the steps taken to prevent moisture loss, the weight-percentages of ingredients in the interior aqueous phase is essentially similar to that present in the aqueous reactant phase.

After the bun is cured, it is sliced across the rise of the foam to yield the finished pads, which are enclosed in moisture and vapor-impermeable packages, such as those formed of metal foil, plastic films or paper-foil, paper-plastic composites. The pads can be packaged individually or a plurality of pads can be placed within a single container. Suitable packaging for premoisturized products is known in the art. For example, see U.S. Pat. Nos. 4,017,002; 3,057,467; and 4,219,129, the disclosures of which are incorporated by reference herein.

The Preferred and Alternate Embodiments Shown in the Drawings

Figure 1:
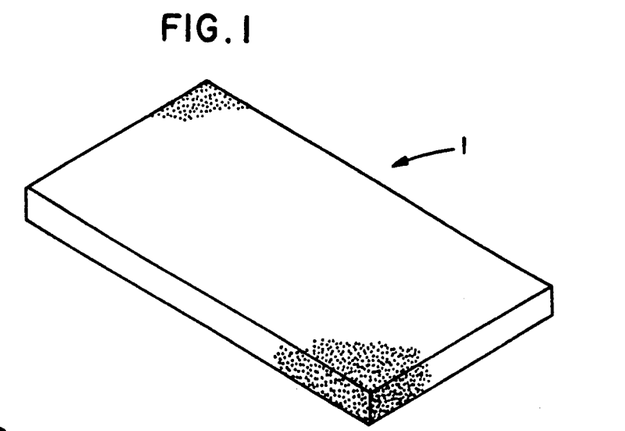
FIG. 1 is a perspective view of a foam pad according to the present invention.

The reference numeral 1, FIG. 1, generally designates a foam pad according to the present invention. Foam pad 1 may be constructed as previously indicated. This construction is such that foam pad 1 comprises a shaped body of foam having an open-celled matrix 2 (indicated by the dotted shading in FIG. 1) which is highly reticulated. Generally, foam pad 1 includes conditioning and styling agents therein, as previously described. Foam pad 1 may optionally also include a temporary hair coloring agent (color not indicated in FIG. 1). Pad 1 is of a generally rectangular configuration. It will be understood, however, that a variety of shapes, sizes, and thicknesses can be readily accommodated in various arrangements and applications according to the present invention.

Figure 2:
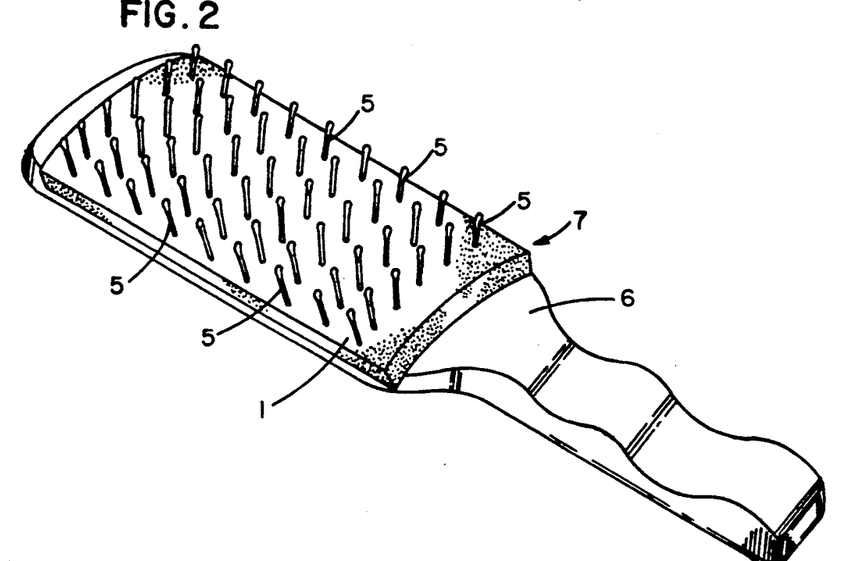
FIG. 2 is a perspective view showing a foam pad of FIG. 1, impaled upon a base or substrate, for use according to the principles of the present invention.

A preferred use of a foam pad, such as pad 1 shown in FIG. 1, is illustrated in FIG. 2 of the drawings. Referring to FIG. 2, foam pad 1 having open-celled matrix 2 is shown impaled upon tine means, in particular tines 5, of a substrate, in particular styling brush 6. Styling brush 6 may be of a conventional design having relatively rigid tines 5 thereon. Pad 1 is placed in a cooperative combination with styling brush 6, simply by pressing pad 1 over tines 5. Generally, pads 1 made according to the present invention will be sufficiently porous for relatively easy mounting upon a conventional substrate such as styling brush 6.

It will be readily understood that a brush/pad combination 7 such as that shown in FIG. 2 can be effectively used for styling, conditioning, or otherwise treating hair, including, optionally, temporarily coloring the hair. As tines 5 of styling brush 6 are passed through the hair in a conventional manner, the hair is brought into contact with pad 1, to apply the conditioning, styling and (optionally) coloring ingredients therein, as previously described. Generally, relatively rigid tines 5 are preferred, for ease of impaling of the pad 1 thereon, and also for effective brushing action in operational contact with the hair of a user. It is noted that the combination may be used to condition and style animal hair as well as human hair.

It will be readily understood that a variety of brush shapes and designs may be used. Thus, for example, the tines may be affixed to a relatively planar support surface, or a curved surface or even be positioned around the outside of a cylindrically shaped brush. Further, pads of a wide variety of shapes and sizes may be particularly developed for use in combination with the corresponding brush shape or size.

It will be further understood that brushes and pads, such as shown in FIG. 2, particularly adapted for use in combination with one another may be provided in a kit form. For example, a kit might include a single brush with a plurality of disposable pads for use in association therewith. Further, such a kit might include a plurality of different types of brushes, for different styling applications, or for use with different types of hair. The kit might also include a plurality of disposable color-modified pads, each impregnated with a different temporary coloring agent.

Figure 3:
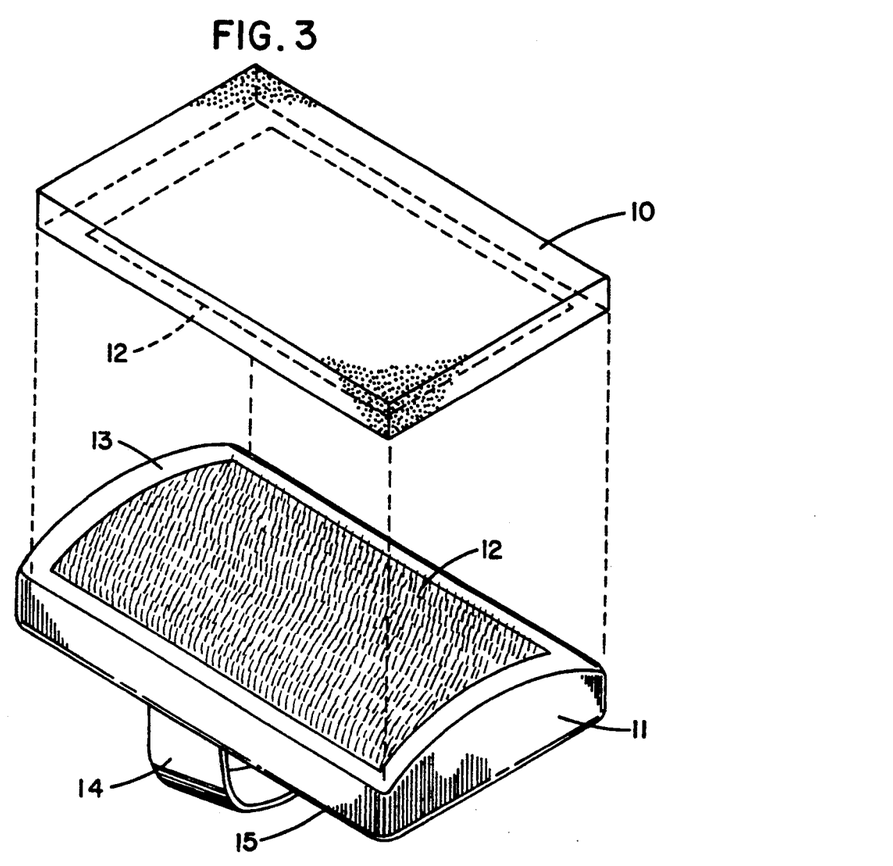
FIG. 3 is an exploded perspective view of a foam pad arrangement according to an alternate embodiment of the present invention.

An alternate embodiment according to the present invention is illustrated in FIG. 3, in which a pad 10 is attached directly to a substrate or handle means, such as base 11 without tine means. Referring to FIG. 3, attachment is provided by means of a hook and loop connection system 12, such as that generally sold under the trade name Velcro ®. It will be understood that a variety of attachment systems may be used, including those involving use of an adhesive or the like. Thus, when desired, pad 10 may be used for hair treatment, which is not accompanied by actual brushing with tines. Preferably, the attachment system is such that a used, such as dirtied, pad can be removed and replaced readily. The embodiment of FIG. 3 may be particularly useful for use in applications involving relatively little hair or fur, or where the skin is particularly sensitive to tines. It is to be understood that pad 10 may optionally also include a temporary coloring agent (color not shown in FIG. 3).

Base 11 illustrated in FIG. 3 is a generally flat base having a slightly concave surface 13, on which pad 10 is mounted. A handle 14, such as a strap or the like, is mounted on the backside 15 of base 11. The strap may be easily grasped, as for example by placing a user's fingers thereunder. It will be understood that while base 11 of FIG. 3 may be preferred for some applications, a variety of base designs may be utilized according to the principles of the present invention.

Figure 4:
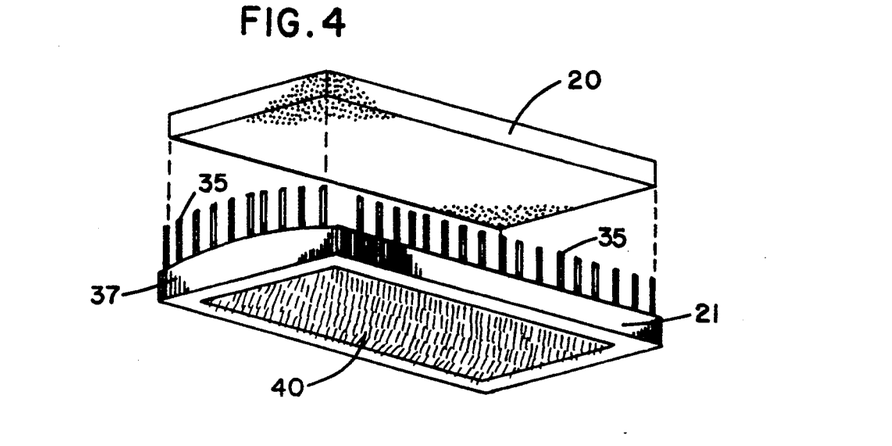
FIG. 4 is an exploded perspective view of a second alternate embodiment of a foam pad arrangement according to the present invention.

Referring to FIG. 4, a second alternate embodiment of the present invention is illustrated. FIG. 4 is an exploded view illustrating components of an alternate embodiment comprising a pad 20 and a removable and replaceable tine means 21. A variety of handle designs may be used.

Pad 20 may be a pad according to the present invention, or any suitable size and shape for the particular brush arrangement involved. Pad 20 may also optionally incorporate a temporary hair coloring agent (color not shown in FIG. 4). Pad 20 is utilized analogously to pad 1 of FIG. 2. That is, pad 20 is impaled upon tines 35 of tine means 21, during use. Tine means 21, unlike the tines of FIG. 2, is readily separable from a base (not shown).

For the arrangement shown in FIG. 4, the tine means comprises a base portion 37 having tines 35 extending outwardly therefrom. The base portion 37 includes means for attachment to a front side of a substrate (not shown). For the embodiment shown in FIG. 4, a hook and loop connection system 40, such as that generally sold under the trade name Velcro ®, is employed. However, it will be understood that a variety of attachment mechanisms, preferably ones which facilitate rapid attachment and disconnection, may be used.

An advantage of an arrangement such as that shown in FIG. 4, is that tine means 21 (and associated tines 35) can be easily removed and replaced, as desired. Thus tines of various lengths, population per given area, rigidity or the like, may be used. It is foreseen that an arrangement such as FIG. 4 may be provided in a kit form, including at least one disposable pad 20, a variety of different, but analogously operating, members with tines 35, and at least one base or substrate on which the pad 20 and the means 21 may be mounted. It will be understood that a variety of shapes or designs of substrates may be used, including ones having straps thereon to provide an overall structure analogous to that shown in FIG. 4, and also including ones (not shown) providing an overall handle arrangement analogous to that shown in FIG. 2.

Figure 5:
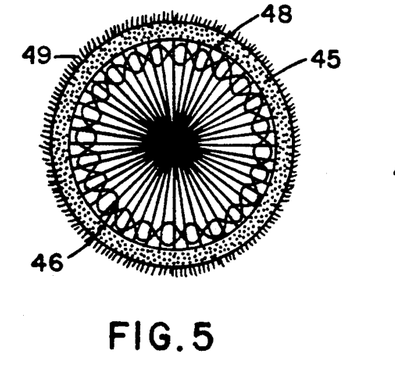
FIG. 5 is an end elevational view of a third alternate embodiment of a foam pad arrangement according to the present invention.
Figure 6:
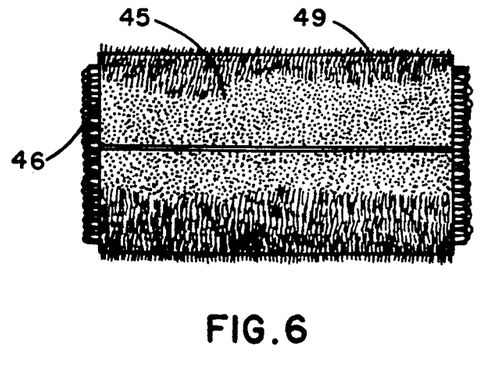
FIG. 6 is a side elevational view of the embodiment shown in FIG. 5.

In FIGS. 5 and 6, a foam pad 45 according to the present invention is shown utilized in association with a hair roller 46. Roller 46 may be of a conventional type. The foam pad/roller combination may be used to effectively curl and condition hair with less likelihood of damage. It is noted that curler 46 may be an electric roller, but it need not be. Pad 45 is wrapped around an outside cylindrical wall 48 of roller 46. In FIGS. 5 and 6, the pad 45 is shown impaled on fine wires 49 of roller 46.

From the figures previously described it will be understood that a wide variety of arrangements utilizing foam pads according to the present invention may be provided. Generally, what is required is a convenient positioning of the foam pad such that it can be brought into contact with the surface or material to be treated. Brush arrangements such as that shown in FIG. 2 may be particularly convenient for use with human hair, or the hair of various animals such as domestic pets. The arrangement in FIG. 3 may be preferred for treating skin surfaces having relatively little hair thereon. The arrangement shown in FIG. 4 may be desired for maximum flexibility for treating hair of various lengths, coarseness, etc.

The invention will be further described by reference to the following detailed examples.

EXAMPLE I

Foam Pad/Brush Composites for Conditioning and Styling

A one-liter beaker equipped with mechanical stirring was charged with 233.5 g of distilled water, the water was heated to 27° C., and 3.45 g of a cationic cellulosic conditioner/styler (Celquat ®, polyquaternium-4, a copolymer of hydroxyethylcellulose and diallyl-dimethyl ammonium chloride, National Starch and Chem. Corp., Bridgewater, N.J.) was sifted in with good agitation. Stirring was continued for 30 min. until a smooth, clear, particulate-free solution was obtained. The reaction mixture was maintained at 27° C. and 3.18 g of pre-melted poloxomer 215 nonionic surfactant (Pluronic ® P-75, BASF-Wyandotte) was slowly added. Mixing was continued for about 5–109 min. until dissolution was complete. Hydrolyzed animal protein (11.43 g of Peptein ® 2000 was added slowly and the reaction mixture was stirred for about 5 min. Hydantoin preservative (2.55 g of Dantogard ®, Glyco, Greenwich, Conn.) was added, and stirring continued for 5 min. Solid sodium chloride (1.60 g) was slowly sifted into the reaction mixture and stirring was continued for about 10 min. until dissolution was complete. Fragrance (1.08 g) was added, and after 5 min. of stirring, 29.7 g of a 50% ethanolic vinylpyrrolidone solution vinyl acetate copolymer (PVP/VA E-635, GAF) was added. After 10 min. of stirring 9.69 g of polyvinylpyrrolidone powder (PVP K-90 GAF) was slowly sifted into the stirred reaction mixture, avoiding the formation of any agglomerates. The reaction mixture was stirred for 30 min. until complete dissolution was achieved. The vinyl-pyrrolidone-alkene copolymer Ganex ® P-904, 6.0 g was slowly sifted into the stirred mixture, stirring for 30 min. until dissolution was achieved and the resultant aqueous reactant phase was stirred for an additional 30 min.

A portion of 150 g of the aqueous reactant phase was poured into a 50 ml beaker and maintained at 25° C. A 37° C. portion of 66.7 g of Hypol ® 3000 prepolymer resin was added and stirring continued for about 10 sec. as the foaming reaction started.

The foaming mixture (275 g) was poured into a rectangular high density polyethylene box (17.5 cm × 12.5 cm × 8.0 cm). The foam bun was covered after full rise was reached and allowed to cure for about 2–4 hours. The cured foam bun exhibited a density of 0.157 g/cc.

The cured bun was sliced with an electric slicer across the rise of the foam and then trimmed to a final dimension of 11.3 cm × 8.0 cm × 0.8 cm. The resilient, moist, open-celled foam pad was then packaged in a plastic-lined paper envelope to prevent loss of the volatile components.

The finished foam pad was easily impaled on the prongs of a hair styling brush, as depicted in FIG. 1. The resulting composite pad/brush was used to comb wet or damp hair as it was blown dry with a hair dryer. The brush was effective to impart a conditioned and styled effect on the hair, and left a pleasant residual odor. When the pad was wrapped around a roller, a composite roller resulted which was effective to impart or restore hair waves. Generally, in association with a roller, the pad heightens the styling, shaping and curl retention effects of the hair dryer or electric roller.

The formulation of this hydrophilic foam pad is summarized in Column A of Table I, below. The formulations listed as Examples I(B)–(G) were prepared as described for Example I, with the exceptions as noted. The ingredients were generally added to the water in the order: Celquat ® H-100, Peptein ® 2000, preservative, fragrance, PVP/VA E635, nonionic surfactant, NaCl, PVP K-90, and Ganex ® P-904. In Example I(B), the order of addition was as follows: Celquat ® H-100, Lanexol ® AWS, Gafquat ® 755 N, triacetin, Dehyquart ® A, Procetyl ® AWS, Peptein ® 2000, Dow Cornin ® 929, preservative and frangrance. In Examples F and G, the order of addition to the water was in the order: Celquat ® H-100, Pluronic ® P-75, Peptein ® 2000, preservative, NaCl, fragrance, PVP/VA E-635, PVP K-90, Ganex ® P-904, Gaffix ® VC-713 and PVP/VA S-630.

TABLE I

| Hydrophilic Foam Pads Formulation of Example I[a] | | | | | |
|---|---|---|---|---|---|
| Component | A | B* | C* | D* | E** |
| Water | 80.05 | 85.70 | 79.42 | 79.40 | 82.06 |
| Nonionic Surfactant[b] | 1.06 | 4.00 | 2.29 | 1.06 | 1.49 |
| Dehyquart ® A cationic surfactant | — | 1.0 | — | — | — |
| Triacetin Plasticizer | — | 5.0 | — | — | — |
| Sodium Chloride | 0.53 | — | — | 0.53 | 0.75 |
| Preservative | 0.34 | 0.32 | 0.33 | 0.34 | 0.34 |
| Fragrance | 0.36 | 0.66 | 0.66 | 0.99 | 0.36 |
| Ethanol[c] | 4.59 | — | 7.42 | 5.34 | 5.20 |
| Conditioning Agent*** | | | | | |
| Celquat ® H-100 | 1.15 | 2.50 | — | 1.15 | — |
| Gafquat ® 755N | — | 0.6 | 1.53 | — | — |
| Peptein ® 2000 | 2.96 | 0.05 | 0.55 | 2.09 | — |
| Dow Corning 929 | — | — | 1.0 | — | — |
| PVP K-90 | 2.0 | — | — | 3.75 | 2.60 |
| PVP/VA E-635 | 4.59 | — | 7.42 | 5.34 | 5.20 |

TABLE I-continued

Hydrophilic Foam Pads
Formulation of Example I[a]

| Ganex ® P-904 | 2.0 | — | — | — | 2.0 |
| --- | --- | --- | --- | --- | --- |

| Component | F* | G* |
| --- | --- | --- |
| Water | 79.75 | 77.79 |
| Nonionic Surfactant[b] | 1.06 | 1.06 |
| Sodium Chloride | 0.53 | 0.53 |
| Preservative | 0.83 | 0.83 |
| Fragrance | 0.15 | 0.15 |
| Ethanol[c] | 4.60 | 5.83 |
| Conditioning Agent*** | | |
| Celquat ® H-100 | 1.15 | 1.15 |
| Peptein ® 2000 | 2.10 | 2.10 |
| PVP/VA E-635 | 4.60 | 4.60 |
| PVP K-90 | 3.23 | 3.23 |
| Ganex ® P-904 | 2.00 | — |
| Gaffix ® VC-713 | — | 0.73 |
| PVP/VA S-630 | — | 2.00 |

[a]Percent active component
[b]Exs. I(A), (D)–(G); Pluronic ® P-75; Ex. I(B). Lanexol ® AWS, 2.0%; Procetyl AWS, 2.0%; Ex. I(C). Pluronic ® P-75, 1.29%, Dow Corning 190, 1.0%
[c]From PVP/VA resin or from Gaffix ® VC-713
*Ratio of aqueous reactant phase: Hypol ® resin was 6:4
**Ratio of aqueous reactant phase: resin was 69.2:30.8
***Includes ingredients commercially referred to as "conditioners," "stylers," or mixtures thereof The pads formed using the formulations of Exs. I(B-)-(G) also performed effectively when affixed to a styling brush or a curling roller to condition and style hair.

EXAMPLE II

Color-Modified Foam Pad/Brush Composite

A one-liter beaker equipped with mechanical stirring was charged with 390.15 g of distilled water, the after was heated to 27° C., and 5.75 g of a cationic cellulosic conditioner (Celquat ® H-100, granular powder, 93% nonvolatiles, polyquaternium-4, National Starch and Chem. Corp., Bridgewater, N.J.) was sifted in with good agitation. Stirring was continued for 30 min. until a smooth, clear, particulate-free solution was obtained, the reaction mixture was maintained at 27° C. and 5.30 g of pre-melted poloxomer 215 nonionic surfactant (Pluronic ® P-75, BASF-Wyandotte) was slowly added. Mixing was continued for about 5-10 min. until dissolution was complete. Hydrolyzed animal protein (19.05 g of Peptein ® 2000, 55% solids, 45% water) was added slowly and the reaction mixture was stirred for about 5 min. Hydantoin preservative (4.25 g of Glydant ®, Glyco, Greenwich, Conn.) was added, and stirring continued for 5 min. Solid, fine sodium chloride (2.65 g) was slowly sifted into the reaction mixture and stirring was continued for about 10 min. until dissolution was complete. Fragrance (0.75 g of 143—046, (Alpine Aromatics)) was added, and after 5 min. of stirring, 45.95 g of a 50% ethanolic vinylpyrrolidone solution vinyl acetate copolymer (PVP/VA E-635, GAF) was added. After 10 min. of stirring, 16.15 g of polyvinylpyrrolidone powder (PVP K-90, GAF) was slowly sifted into the stirred reaction mixture, avoiding the formation of any agglomerates. The reaction mixture was stirred for 30 min. until complete dissolution was achieved. The vinyl-pyrrolidone-alkene copolymer, Ganex ® P-904, 10.0 g, was slowly sifted into the stirred reaction mixture, and stirred for 30 min. until dissolution was achieved. Then 15.0 g of temporary hair coloring agent (7054 Cosmetic Iron Oxide Red; Whittaker, Clark & Daniels) was slowly sifted into the stirred reaction mixture, and stirred for an additional 30 min. until a complete and even dispersion of the color was achieved. The resultant aqueous reactant phase was then stirred for an additional 30 min. After stirring was completed, the aqueous phase was of a uniform deep red or auburn color.

A portion of 34.60 g of the aqueous reactant phase was poured into a 500 ml beaker and maintained at 27° C. A 37° C. portion of 15.40 g of Hypol ® 3000 prepolymer resin was added, and stirring continued for about 10 sec. as the foaming reaction started.

The foaming mixture (50 g) was poured into a rectangular high density polyethylene box (17.5 cm × 12.5 cm × 8.0 cm). The foam bun was covered after full rise was reached and allowed to cure for about 2-4 hours. The cured foam bun exhibited a density of 0.160 g/cc, and was uniformly deep red or auburn in color.

The cured bun was sliced with an electric slicer across the rise of the foam and then trimmed to a final dimension of 11.3 cm × 8.0 cm × 0.8 cm. The resilient, moist, open-celled foam pad was then packaged in a plastic-lined paper envelope to prevent loss of the volatile components.

The finished foam pad was easily impaled on the prongs of a hair styling brush, as depicted in FIG. 1. The resulting composite pad/brush was used to comb wet or damp hair as it was blown dry with a hair dryer. The natural color of the user's hair prior to application of the foam pad was light brown. The pad/brush was effective to impart a red or auburn color to the hair, imparted a conditioned and styled effect on the hair, and left a pleasant residual odor. The red color was removed from the user's hair by a single subsequent shampooing. After the shampooing, the user's hair was in its natural light brown color.

The formulation of this hydrophilic foam pad is summarized in Column A of Table II, below. The formulations listed as Examples II(B)-(D) were prepared as described for Example II, with the exceptions as noted. The ingredients were generally added to the water in the order: Celquat ® H-100 or L-200, nonionic surfactant, Peptein ® 2000, preservative, NaCl, fragrance, PVP/VA E-635, PVP K-90, Ganex ® P-904 and temporary hair coloring agent.

TABLE II

Hydrophilic Color-Modified Foam Pads
Formulation of Example II[a]

| Component | A | B | C | D |
| --- | --- | --- | --- | --- |
| Water | 69.84 | 69.84 | 69.66 | 69.66 |
| Nonionic Surfactant[b] | 0.93 | 0.93 | 0.93 | 0.93 |
| Sodium Chloride | 0.46 | 0.46 | 0.46 | 0.46 |
| Preservative | 0.74 | 0.74 | 0.74 | 0.74 |
| Fragrance | 0.13 | 0.13 | 0.31 | 0.31 |
| Ethanol[c] | 4.02 | 4.02 | 4.02 | 4.02 |
| Color[d] | 12.5 | 12.5 | 12.5 | 12.5 |
| Conditioning Agent[e] | | | | |
| Celquat ® H-100 | 0.94 | 0.94 | 0.94[f] | 0.94[f] |
| Peptein ® 2000 | 1.84 | 1.84 | 1.84 | 1.84 |
| PVP K-90 | 2.83 | 2.83 | 2.83 | 2.83 |
| PVP/VA E-635 | 4.02 | 4.02 | 4.02 | 4.02 |
| Ganex ® P-904 | 1.75 | 1.75 | 1.75 | 1.75 |

[a]Percent active component
[b]Pluronic ® P-75
[c]From PVP/VA E-635 resin
[d]Formulation A, 7054 Cosmetic Iron Oxide Red (Whittaker, Clark & Daniels); Formulation B, 7055 Cosmetic Iron Oxide Yellow (Whittaker, Clark & Daniels); Formulation C, Chroma-Lite ® Red (Van Dyk); Formulation D, Spectra-Pearl ® RDW (Van Dyk)
[e]Includes ingredients commercially referred to as "conditioners," "stylers," or mixtures thereof
[f]Celquat L-200 used instead of H-100
Ratio of aqueous reactant phase: Hypol ® resin was 2.25:1 in all formulations The invention has been described with reference to various specific and preferred embodiments and techniques. However, it should be understood that many variations and modifications may be made while remaining within the spirit and scope of the invention.

What is claimed is:

1. A hair conditioning and styling pad consisting essentially of a resilient, open-celled, hydrophilic polyurethane foam matrix, wherein bound to said matrix is an aqueous phase incorporating about 70–90% water, about 5–25% of a polymeric organic film-forming hair conditioning agent and about 0.1–10% of a nonionic surfactant, wherein said aqueous phase does not include a significant amount of water-immiscible organic solvent.

2. The pad of claim 1 wherein the nonionic surfactant comprises a water-soluble polyoxyalkylene block copolymer.

3. The pad of claim 2 wherein the copolymer comprises a polyoxypropylene ether having a molecular weight of about 1750–2250 and a polyoxyethylene content which is about 40–60% of the copolymer by weight.

4. The pad of claim 3 wherein the surfactant further comprises about 0.25–5% of a silicone glycol copolymer.

5. The pad of claim 1 wherein the aqueous phase further comprises about 0.5–2.5% of an inorganic alkali metal or alkaline earth metal salt.

6. The pad of claim 1 wherein the hair conditioning agent comprises a cationic organic polymer.

7. The pad of claim 6 wherein the hair conditioning agent comprises collagen or a collagen derivative.

8. The pad of claim 6 wherein the hair conditioning agent comprises a cationic cellulosic polymer.

9. The pad of claim 6 wherein the hair conditioning agent comprises a vinylpyrrolidone-based polymer or copolymer.

10. The pad of claim 1 which further comprises a minor but effective amount of fragrance.

11. A hair conditioning and styling pad consisting essentially of a resilient, open-celled, hydrophilic polyurethane foam matrix, wherein bound to said matrix, is an aqueous phase incorporating about 75–85% water, about 10–20% of a polymeric organic film-forming, hair conditioning agent, about 0.25–5% of a nonionic surfactant, and an amount of an inorganic salt effective to substantially enhance the release of the aqueous phase from the foam matrix when the pad is pressed against the hair, wherein said aqueous phase does not include a significant amount of water-immiscible organic solvent.

12. The pad of claim 11 wherein the cells of said pad substantially vary in diameter.

13. The pad of claim 11 wherein a substantial number of said cells are about 1.0–5.0 mm in diameter.

14. The pad of claim 11 wherein the aqueous phase further comprises about 1–20% of a particulate soft mineral absorbent which is silane-coupled to the foam matrix.

15. The pad of claim 11 wherein the aqueous phase further comprises a minor but effective amount of a topically active insecticide or a minor but effective amount of an antidandruff agent.

16. The pad of claim 11 wherein the aqueous phase further comprises a minor but effective amount of fragrance.

17. The pad of claim 11 wherein the hair conditioning agent comprises hydrolyzed animal protein or a derivative thereof.

18. The pad of claim 11 wherein the hair conditioning agent comprises a cationic polymer.

19. The pad of claim 18 wherein the hair conditioning agent comprises a cationic cellulosic polymer.

20. A hair styling and conditioning pad formed by a process comprising:
(a) forming an aqueous reactant phase comprising a dispersion in about 70–90% water of about 5–25% of a polymeric organic film-forming hair conditioning agent and about 0.1–10% of a nonionic surfactant comprising a polyoxalkylene block copolymer of a mixture of a polyoxyalkoxylated lanolin and a polyoxyalkoxylated fatty alcohol, wherein said aqueous reactant phase does not include a significant amount of water-immiscible organic solvent; and
(b) mixing said aqueous reactant phase with a water-foamable prepolymer resin which contains at least 2 free isocyanate groups per resin molecule in a weight ratio of aqueous reactant phase to prepolymer resin of about 3.0–1.0:1, thereby forming said resin into a hydrophilic, open-celled, highly reticulated polyurethane foam pad.

21. The pad of claim 20, wherein in step (b) the final mole ratio of water to total free resin isocyanate groups is about 20–150:1.

22. The pad of claim 20 wherein the aqueous phase further comprises about 1–20% of a particulate mineral absorbent and about 0.1–5% by weight of said absorbent of a silane-coupling agent.

23. The pad of claim 20 wherein said hair conditioning agent comprises a cationic cellulosic polymer.

24. The pad of claim 20 wherein said hair conditioning agent comprises collagen or a collagen derivative.

25. The pad of claim 20 wherein said hair conditioning agent comprises a vinylpyrrolidone-based polymer or copolymer.

26. The pad of claim 20 wherein the aqueous reactant phase comprises 0.5–2.5% of an inorganic alkali metal or alkaline earth metal salt.

27. An assembly for treatment of hair or the like; said assembly comprising:
(a) a base member; and
(b) a pad member mounted on said base member; said pad member comprising a resilient, open-celled, hydrophilic polyurethane foam matrix, wherein bound to said matrix is an aqueous phase incorporating about 70–90% water, about 5–25% of a polymeric organic film-forming hair conditioning agent and about 0.1–10% of a nonionic surfactant, wherein said aqueous phase does not include a significant amount of water-immiscible organic solvent.

28. An assembly according to claim 27 including tine means projecting outwardly from said pad member.

29. An assembly according to claim 27 wherein:
(a) said base member comprises a brush having a plurality of tines projecting outwardly therefrom; and,
(b) said pad member is impaled upon said plurality of tines.

30. An assembly according to claim 27 wherein said base member is a hair roller.

31. A kit for providing styling and conditioning of hair; said kit including:

(a) at least one base member; and
(b) at least one pad member mountable on said base member; said pad member comprising a resilient, open-celled, hydrophilic polyurethane foam matrix, wherein bound to said matrix is an aqueous phase incorporating about 70-90% water, about 5-25% of a polymeric organic film-forming hair conditioning agent and about 0.1-10% of a nonionic surfactant, wherein said aqueous phase does not include a significant amount of organic solvent.

32. A kit according to claim 31 wherein:
(a) said base member comprises a brush having a plurality of tines projecting outwardly therefrom; and
(b) said pad member is operably impalable on said plurality of tines.

33. The kit according to claim 31 wherein the base member comprises a hair roller.

34. A method of styling and conditioning hair; said method comprising:
(a) providing an assembly comprising a base member with a pad member mounted thereon; said pad member comprising a resilient, open-celled hydrophilic polyurethane foam matrix, wherein bound to said matrix is an aqueous phase incorporating about 70-90% water, about 5-25% of a polymeric organic film-forming hair conditioning agent and about 0.1-10% of a nonionic surfactant, wherein said aqueous phase does not include a significant amount of organic solvent; and
(b) manipulating said base member to bring said pad member into contact with hair to be styled and conditioned.

35. The method according to claim 34 including the steps of:
(a) providing tine means projecting outwardly from said pad member; and
(b) brushing said tine means through the hair to be styled and conditioned.

36. The method according to claim 34 wherein:
(a) said base member comprises a brush having a plurality of tines projecting outwardly therefrom; and
(b) said pad member is impaled upon said plurality of tines.

37. The method according to claim 34 wherein said base member comprises a hair roller.

* * * * *